United States Patent [19]
Kawajiri et al.

[11] Patent Number: 5,198,581
[45] Date of Patent: Mar. 30, 1993

[54] PROCESS FOR PRODUCING UNSATURATED ALDEHYDES AND UNSATURATED ACIDS

[75] Inventors: Tatsuya Kawajiri; Hideyuki Hironaka; Shinichi Uchida, all of Himeji; Yukio Aoki, Hyogo, all of Japan

[73] Assignee: Nippon Shokubai Co., Ltd., Osaka, Japan

[21] Appl. No.: 679,319

[22] Filed: Apr. 2, 1991

[30] Foreign Application Priority Data
Apr. 3, 1990 [JP] Japan .................... 2-87355

[51] Int. Cl.$^5$ ............................ C07C 27/14
[52] U.S. Cl. .................... 562/546; 562/537; 562/538
[58] Field of Search .............. 562/546, 537, 538

[56] References Cited
U.S. PATENT DOCUMENTS
4,837,360  6/1989  Kadowaki et al. .............. 562/546

FOREIGN PATENT DOCUMENTS
3006894  9/1980  Fed. Rep. of Germany.
1529384  10/1978  United Kingdom.
2063861A  6/1981  United Kingdom.

Primary Examiner—Arthur C. Prescott
Attorney, Agent, or Firm—Sherman and Shalloway

[57] ABSTRACT

A process for producing an unsaturated aldehyde or an unsaturated acid comprises catalytically oxidizing propylene or at least one compound selected from isobutylene, tert.-butyl alcohol and methyl-tert.-butyl ether in a gaseous phase with molecular oxygen or a molecular oxygen-containing gas using a fixed bed multipipe reactor, wherein (a) a plurality of composite oxides, different in occupied volume, are used as catalyst, (b) a plurality of reaction zones are provided along an axial direction in each reaction pipe of the fixed bed multipipe reactor, and (c) the plurality of the catalysts different in occupied volume are filled in the plurality of the reaction zones such that the occupied volumes become lower from the starting gas inlet side to the outlet side.

8 Claims, No Drawings

PROCESS FOR PRODUCING UNSATURATED ALDEHYDES AND UNSATURATED ACIDS

This invention relates to a process for producing an unsaturated aldehyde and an unsaturated acid. More specifically, this invention relates to a process for producing an unsaturated aldehyde and an unsaturated acid, i.e. acrolein and acrylic acid or methacrolein or methacrylic acid by catalytically oxidizing propylene or at least one compound selected from isobutylene, tert.-butyl alcohol and methyl-tert.-butyl ether with molecular oxygen or a molecular oxygen-containing gas in a gaseous phase using a fixed bed multipipe reactor.

A great many composite oxide catalysts containing molybdenum, bismuth and iron have been already proposed for catalytically oxiding $C_{3-4}$ olefins in a gaseous phase to produce corresponding unsaturated aldehydes and unsaturated acids, and some of them have been used industrially. Typical examples are described in Japanese Patent Publication Nos. 42241/1972, 42242/1972, 22490/1972, 45256/1980, 61011/1982, 23370/1983 and 49535/1983, and Japanese Laid-open Patent Application Nos. 73488/1978 and 31727/1984.

Nevertheless, industrial production of unsaturated aldehydes or unsaturated aldehydes and unsaturated acids using these catalysts give rise to various problems.

One problem is generation of an abnormal local high-temperature portion (hot spot) in a catalyst layer. For instance, it is industrially demanded to increase productivity of a final product; to meet this demand, generally, a concentration of a starting olefin is increased or a space velocity is raised. However, under such high load reaction conditions, a hot spot occurs in a catalyst layer because the catalytic reaction in the gaseous phase is an exothermic reaction, with the result that a hot spot occurs in the catalyst layer and an excessive oxidation reaction occurs. On this occasion, the catalyst is degraded in the hot spot by the excessive heat generation, and in the worst case, a violent reaction is invited.

In order to suppress occurrence of the hot spot or accumulation of heat in the hot spot, productivity has to be kept low or a reaction pipe is made to have a small diameter. These measures are however not said to be commercially advantageous.

There are provided a process in which a catalyst in a hot spot is diluted with an inactive substance (see Japanese Patent Publication No. 9859/1959, 24403/1968 and 30688/1978, and Japanese Laid-open Patent Application No. 127013/1976), a process in which a catalyst for oxidation of propylene or isobutylene and/or tert.-butyl alcohol is made ring-like (see Japanese Patent Publication Nos. 36739/87 and 36740/1987), a process in which in the oxidation reaction of propylene or isobutylene, two reaction zones are provided in a reaction pipe (see Japanese Laid-open Patent Application No. 127013/1976), and a process in which in the oxidation of propylene, a plurality of catalysts obtained by varying a composition (especially a type and/or an amount of an alkali metal) and having various controlled activities are filled dividedly along an axis of a reaction pipe in the order of a higher activity from a starting gas inlet side toward an outlet side (see Japanese Patent Publication No. 38331/1988).

However, in the process to dilute the catalyst with the inactive substance, it takes much labor to uniformly mix the diluting inactive substance with the catalyst and they cannot be altogether uniformly mixed, so that a hot spot tends to occur. Besides, a position and a temperature of the hot spot are different in the individual reaction pipes which is inconvenient in the operation of the reaction. Accordingly, said process is not said to be satisfactory as a process to suppress the hot spot.

The process to control the activity of the catalyst by making it ring-like cannot be said either as a sufficient process to control a hot spot under high load reaction conditions, i.e. under conditions of a high concentration of a starting material and a high space velocity.

In the process to control the activity of the catalyst by varying the type and/or the amount of the alkali metal, the amount of the catalyst added is far smaller than those of the other ingredients and the effect of the catalyst added is great, so that much care should be taken in preparing the catalyst. Moreover, in reality, the activity of the catalyst does not become desirable by the influence of alkali metals and/or alkaline earth metals contained in larger amounts of other starting materials.

Upon solving the aforesaid problems in the prior art, this invention aims to provide a process for producing with good efficiency acrolein and acrylic acid from propylene, or methacrolein and methacrylic acid from at least one compound selected from isobutylene, tert.-butyl alcohol and methyl-tert.-butyl ether.

It is an object of this invention to provide a process which can produce in high yields acrolein and acrylic acid, or methacrolein and methacrylic acid by catalytically oxidizing propylene, or at least one compound selected from isobutylene, tert.-butyl alcohol and methyl-tert.-butyl ether in a gaseous phase.

Another object of this invention is to provide a process in which when producing acrolein and acrylic acid from propylene, or methacrolein and methacrylic acid from at least one compound selected from isobutylene, tert.-butyl alcohol and methyl-tert.-butyl ether in a gaseous phase, accumulation of a heat in a hot spot can be suppressed to improve yields of the unsaturated aldehydes and the unsaturated acids and degradation of the catalyst can be prevented to use the catalyst stably for a long period of time.

Still another object of this invention is to provide a process in which when catalytically oxidizing propylene or at least one compound selected from isobutylene, tert.-butyl alcohol and methyl-tert.-butyl ether in a gaseous phase, accumulation of a heat in a hot spot can be suppressed even under high load reaction conditions, and acrolein and acrylic acid, or methacrolein and methacrylic acid can be produced with high productivity.

In the exothermic reaction such as the gaseous phase catalytic oxidation in this invention, it has been hitherto considered that when a size of catalysts used is increased, heat conduction between the catalysts is prevented and a temperature of hot spots is rather raised. In accordance with the present inventor's research works, it has however been found that when the size of the catalysts is increased, the temperature of the hot spots is lowered and that the object can be achieved when a plurality of catalysts different in size (i.e. different in occupied volume) are disposed in a reaction zone divided in plural portions along an axial direction of a reaction pipe in the order of a smaller size from a starting gas inlet side toward an outlet side.

Thus, according to this invention, there is provided a process for producing an unsaturated aldehyde and an unsaturated acid by catalytically oxidizing propylene or at least one compound selected from isobutylene, tert.- butyl alcohol and methyl-tert.-butyl ether in a gaseous phase with molecular oxygen or a molecular oxygen-containing gas using a fixed bed multipipe reactor, characterized in that (a) a plurality of composite oxides different in occupied volume, represented by formula $$Mo_aW_bBi_cFe_dA_eB_fC_gD_hO_x \qquad (I)$$

wherein Mo denotes molybdenum; W denotes tungsten; Bi denotes bismuth; Fe denotes iron; A denotes at least one element selected from cobalt and nickel; B denotes at least one element selected from an alkali metal, an alkaline earth metal and thallium; C denotes at least one element selected from phosphorus, tellurium, arsenic, boron, niobium, antimony, tin, lead, manganese, cerium and zinc; D denotes at least one element selected from silicon, alminum, titanium and zirconium; O denotes oxygen; a, b, c, d, e, f, g, h and x denote numbers of atoms of Mo, W, Bi, Fe, A, B, C, D and O; when $a=2$ to 12, $b=0$ to 10 and $a+b=12$, $c=0.1$ to 10, $d=0.1$ to 10, $e=2$ to 20, $f=0.005$ to 3, $g=0$ to 4, $h=0.5$ to 30 and $x=$value determined by an oxidized state of each element,
are used as catalysts, (b) a plurality of reaction zones are provided along an axial direction in each reaction pipe of the fixed bed multipipe reactor, and (c) the plurality of the catalysts different in occupied volume are filled in the plurality of the reaction zones such that the occupied volumes become lower from the starting gas inlet side to the outlet side.

The starting material used in this invention is propylene or at least one compound selected from isobutylene, tert.-butyl alcohol and methyl-tert.-butyl ether. That is, according to one embodiment of this invention, acrolein and acrylic acid can be produced by catalytically oxidizing propylene in a gaseous phase. According to another embodiment of this invention, methacrolein and methacrylic acid can be produced by catalytically oxidizing at least one compound selected from isobutylene, tert.-butyl alcohol and methyl-tert.-butyl ether.

In this invention, the fixed bed multipipe reactor is used, and a plurality of reaction zones (portions filled with catalysts, i.e. catalyst layers) are provided along an axial direction in each reaction pipe. The larger the number of the reaction zones, the better the results. About 2 to 5 reaction zones are industrially sufficient.

A suitable length or a suitable length ratio of each reaction zone varies with a size of a catalyst being filled; it may properly be determined to obtain an optimum yield as a whole. An inner diameter of each reaction pipe is about 15 to 40 mm.

In this invention, it is important that the plurality of the composite oxides of formula (I) different in size, i.e. in occupied volume are prepared as catalysts, and these catalysts are filled in the plurality of the reaction zones such that the occupied volumes become lower from the starting gas inlet side to the outlet side.

The shape of the catalyst used in this invention is not particularly limited and may be spherical, cylindrical (pellet-like) or ring-like. The spherical shape is not necessarily round, but may be substantially spherical. This holds true of the cylindrical or ring-like shape.

What this invention terms the "occupied volume" means a space in which each catalyst particle occupies when the catalyst is filled in the reaction zone. To be concrete, when the catalyst particle is spherical, its occupied volume (V) is represented by the equation, $$V=(4/3)\times\pi\times(R/2)^3 \; (mm^3)$$

wherein R (mm) is a diameter.

Thus, in case of the spherical catalyst, catalysts different in occupied volume can be prepared by varying the diameter (R). Especially, spherical catalysts prepared by varying the diameter (R) within the range of 3 to 15 mm are preferably used in this invention.

In case of the cylindrical catalyst particle, its occupied volume is represented by the equation, $$V=\pi\times(R/2)^2\times L \; (mm^3)$$

wherein R (mm) is a diameter, and L is a length.

Thus, in case of the cylindrical catalyst, catalysts different in occupied volume can be prepared by varying the diameter (R) and/or the length (L). Especially, cylindrical catalysts prepared by varying the diameter (R) and/or the length (L) within the range of 3 to 15 mm are preferably used in this invention.

In case of the ring-like catalyst particle, its occupied volume is represented by the equation, $$V=\pi\times(R'/2)^2\times L'(mm^3)$$

wherein R' is an outer diameter, and L' (mm) is a height of a ring.

Thus, in case of the ring-like catalyst, catalysts different in occupied volume can be prepared by varying the outer diameter (R') and/or the height (L') of the ring. Especially, ring-like catalysts prepared by varying the outer diameter (R') and/or the height (L') of the ring within the range of 3 to 15 mm are preferably used in this invention.

In the ring-like catalyst, the diameter (i.e. the inner diameter) of the hollow portion does not influence the occupied volume and can take any value.

In the spherical, cylindrical or ring-like catalyst, when the diameter (R), the outer diameter (R'), the length (L) and the ring height (L') are less than 3 mm, the catalyst particles are too small and the temperature of the hot spot tends to rise. Meanwhile, when they are more than 15 mm, the catalyst particles are too large to be filled in the reaction pipe; even if selectivity is raised, conversion of the starting material decreases and as a result, the yield of the final compound is liable to decrease.

By the way, the diameter (R), the outer diameter (R'), the length (L) and the ring height (L') are average values of a diameter, an outer diameter, a length and a ring height of catalyst particles filled in each reaction zone. Also, the occupied volume in this invention is an average value of an occupied volume of catalyst particles filled in each reaction zone.

In this invention, when filling the plurality of the catalysts different in occupied volume in the plurality of the reaction zones such that the occupied volumes become lower from the starting material inlet side toward the outlet side, it is especially desirable from the aspect of preventing heat accumulation in the hot spot that a ratio of the occupied volumes in the two adjacent reaction zones is within a specific range.

For example, assuming that out of the two adjacent reaction zones, the occupied volume of the reaction zone closer to the starting gas inlet side is made $V_1$ and the occupied volume of the reaction zone closer to the outlet side is made $V_2$, it is advisable that $V_1/V_2$ is 1.2/1 to 64/1. Usually, $V_1/V_2 = 1.3/1$ to 7/1.

Where $V_1/V_2$ is lower than 1.2/1, heat accumulation of the hot spot cannot be prevented enough. While it is higher than 64/1, productivity has to be kept low for prevention of occurrence of the hot spot in the reaction zone with the lower occupied volume and of heat accumulation of the hot spot, and a pressure loss in the reaction zone is great.

In this invention, the compositions of the plurality of the catalysts filled in the plurality of the reaction zones may be the same or different within the range of formula (I).

In this invention, the shapes of the plurality of the catalysts filled in the plurality of the catalyst zones may be the same or different. For instance, when the number of the reaction zones is 2, the catalysts different in shape can be used in combination, such as spherical and cylindrical catalysts, spherical and ring-like catalysts or cylindrical and ring-like catalysts. It is also possible that catalysts different in shape can be used in combination in the same reaction zone, but it is usually advisable that catalysts of the same shape are filled in the same reaction zone.

In accordance with this invention, the plurality of the catalysts comprising the composite oxides of formula (I) and having different occupied volumes are filled in the plurality of the reaction zones such that the occupied volumes become lower from the starting gas inlet side toward the outlet side, whereby occurrence of the hot spot or heat accumulation in the hot spot can be suppressed, reactivity can be increased at the inlet side without decreasing selectivity and the reaction can be completed at the outlet side.

Further, a pressure loss between the inlet and the outlet of the reaction pipe can be decreased, making it possible to achieve energy savings such as reduction of cost of an electric power in a blower, etc.

Still further, the hot spot is dispersed and the temperature of the hot spot is decreased, so that decrease in catalytic activity is stopped and a so-called running cost can be reduced, as well as an effect of prolonging a catalyst life can also be provided.

Usually, when the molybdenum-containing catalyst is used in the reaction, the molybdenum component is easily reduced and sublimed. The sublimation is easier to occur at a higher temperature and a higher steam partial pressure in the starting gas. Accordingly, the amount of molybdenum sublimed in or near the hot spot is large, thereby greatly decreasing the catalytic activity. On the other hand, in this invention, since the hot spot is dispersed and the temperature of the hot spot is decreased, sublimation of the molybdenum component is prevented, degradation of the catalyst is prevented and the catalyst life is thus prolonged.

The catalyst in this invention can be prepared using a method and starting materials commonly employed for preparation of this type of the catalyst. For example, a final catalyst can be prepared by mixing compounds containing respective element components of formula (I), e.g. ammonium salts and nitric acid salts either as such or in the form of an aqueous solution, well kneading the mixture, drying it by heating, and burning the dried product at a temperature of about 350° to 600° C.

A molding method of the catalyst is not limited in particular; extrusion molding or pelleting is available. In a certain case, the composite oxide of formula (I) may be supported on an inactive porous carrier as a catalytic component. The inactive porous carrier may be any inactive porous substance or any substance that can be pulverized in porous state. Examples thereof are alpha-alumina, silicon carbide, pumice, silica, zirconium oxide and titanium oxide.

In this invention, the modes of the plurality of the catalysts filled in the plurality of the reaction zones may be the same or different. For example, when the number of the reaction zones is 2, a combination of a molded catalyst and a supported catalyst can be used.

The gaseous phase catalytic oxidation reaction in this invention may be either an ordinary once-through method or a recycling method, and can be carried out under conditions generally used in this type of the reaction. For example, the oxidation reaction is performed by introducing a gas mixture comprising 1 to 10% by volume of propylene or at least one compound selected from isobutylene, tert.-butyl alcohol and methyl-tert.-butyl ether, 3 to 20% by volume of molecular oxygen, 0 to 60% by volume of steam and 20 to 80% by volume of an inert gas (nitrogen or a carbon dioxide gas) onto the catalysts at a temperature of 250° to 450° C. under pressure of atmospheric pressure to 10 atm at a space velocity of 300 to 5,000 $hr^{-1}$ (STP).

In accordance with this invention, occurrence of the hot spot or heat accumulation of the hot spot can effectively be suppressed even under high load reaction conditions of elevating the concentration of the starting material and increasing the space velocity, so that markedly good results can be obtained in comparison to the ordinary processes.

The following effects can be brought forth by providing in sequence the plurality of the catalysts comprising the composite oxides of formula (I) and having different occupied volumes in the plurality of the reaction zones disposed in the reaction pipes along the pipe axial direction such that the occupied volumes become lower from the starting gas inlet side to the outlet side.

(a) Occurrence of the hot spot or heat accumulation in the hot spot can be suppressed.

(b) An excessive oxidation reaction in the hot spot is prevented, and the final unsaturated aldehydes and unsaturated acids can be obtained with high selectivity in high yields.

(c) Degradation of the catalyst by a heat load is prevented, and the catalyst can be stably used for a long period of time.

(d) The final unsaturated aldehydes and unsaturated acids can be produced under high load reaction conditions of a high concentration of a starting material and a high space velocity, making it possible to greatly increase reactivity.

(e) A pressure loss of a catalyst layer can be kept low.

Consequently, the process of this invention is quite useful to produce the unsaturated aldehydes and the unsaturated acids, i.e. acrolein and acrylic acid, or methacrolein and methacrylic acid.

The following Referential Examples, Examples and Comparative Examples illustrate this invention more specifically.

Conversion, selectivity, one-pass yield and a contact time in this invention are defined as follows.

$$\text{Conversion (mol \%)} = \frac{\text{Number of mols of reacted starting material}}{\text{Number of mols of supplied starting material}} \times 100$$

$$\text{Selectivity (mol \%)} = \frac{\text{Number of mols of formed unsaturated aldehyde and unsaturated acid}}{\text{Number of mols of reacted starting material}} \times 100$$

$$\text{Total yield (mol \%)} = \frac{\text{Number of mols of formed unsaturated aldehyde and unsaturated acid}}{\text{Number of mols of supplied starting material}} \times 100$$

$$\text{Contact time (sec)} = \frac{\text{Apparent volume of filled catalyst (liter)}}{\text{Flow rate of staring gas (liter/hr)*}} \times 3,600$$

*0° C., 1 atm.

REFERENTIAL EXAMPLE 1

[Production of a catalyst]

While heating 4,500 ml of a distilled water with stirring, 2,124 g of ammonium molybdate and 648 g of ammonium paratungstate were dissolved therein to obtain an aqueous solution (A).

Separately, 1,400 g of cobalt nitrate was dissolved in 500 ml of a distilled water to form an aqueous solution (B), 486 g of ferric nitrate was dissolved in 400 ml of a distilled water to form an aqueous solution (C), and 584 g of bismuth nitrate was dissolved in 600 ml of a distilled water acidified with 120 ml of conc. nitric acid to form an aqueous solution (D). The aqueous solutions (B), (C) and (D) were mixed, and the mixed solution was added dropwise to the aqueous solution (A) while vigorously stirring the aqueous solution (A). Successively, an aqueous solution obtained by dissolving 542 g of a silica sol containing 20% by weight of silicon dioxide and 4.04 g of potassium hydroxide in 200 ml of a distilled water was added thereto.

The formed suspension was evaporated to dryness while heating it with stirring, and the resulting product was pulverized and sieved to obtain a powder having a particle diameter of about 150 micrometers.

Then, granulation was performed in accordance with a centrifugal flow-coating method described in Japanese Laid-open Patent Application No. 85139/1989 (see Example I-1-1 thereof). That is, alpha-alumina spherical particles having an average diameter of 1 mm were charged in a centrifugal flow-coating device. Subsequently, using part of the above powder and a distilled water as a binder, spherical particles having an average diameter of 5 mm were formed through hot air of 90° C. After the particles were dried overnight at 120° C., the dried particles were burned at 450° C. for 6 hours under passage of air to obtain a catalyst (1). Said catalyst had the following composition (at an atomic ratio except oxygen).

$Mo_{10}W_2Bi_1Fe_1Co_4K_{0.06}Si_{1.5}$

Part of the above powder was molded with an average diameter of 8 mm in the same way as above, and then burned to obtain a catalyst (2).

The sizes and the occupied volumes of the catalysts (1) and (2) are shown in Table 4 along with those of catalysts (3) to (17) to be described later.

[Oxidation reaction]

A stainless steel (SUS-304) reaction pipe having an average diameter of 25 mm and fitted with a jacket for circulating a molten salt as a heating medium and a thermocouple for measuring a temperature of a catalyst layer was filled with 1,300 ml of the catalyst (2). While keeping the temperature of the molten salt at 320° C., a gas mixture comprising 6% by volume of propylene, 10.2% by volume of oxygen, 5% by volume of steam and 78.8% by volume of nitrogen was passed for a contact time of 2.2 seconds to conduct the reaction.

A pressure loss of the catalyst layer during the reaction, a temperature of a hot spot and a yield were found, and the results are shown in Table 1.

REFERENTIAL EXAMPLE 2

Referential Example 1 was repeated except that a gas mixture comprising 9% by volume of propylene, 15% by volume of oxygen, 10% by volume of steam and 66% by volume of nitrogen was used as a starting gas. The results are shown in Table 1.

REFERENTIAL EXAMPLE 3

Referential Example 1 was repeated except that the catalyst (1) was used instead of the catalyst (2) and the reaction temperature was changed into 310° C. The results are shown in Table 1.

REFERENTIAL EXAMPLE 4

Referential Example 2 was repeated except that the catalyst (1) was used instead of the catalyt (2) and the reaction temperature was changed into 290° C. The results are shown in Table 1.

REFERENTIAL EXAMPLE 5

Referential Example 1 was repeated except that the catalyst (1) was used instead of the catalyst (2), the reaction temperature was changed into 350° C., and a gas mixture comprising 7% by volume of isobutylene, 13.2% by volume of oxygen, 10% by volume of steam and 69.8% by volume of nitrogen was used as a starting gas. The results are shown in Table 1.

The temperature of the hot spot became quite high. Even when the reaction temperature was lowered to 290° C., the temperature of the hot spot was gradually elevated and the reaction was hardly conducted. Moreover, in case of the catalyt (2), the concentration of isobutylene was raised to increase productivity. Then, the reaction could not continue.

EXAMPLE 1

The starting gas outlet portion of the same reactor as used in Referential Example 1 was filled with 650 ml of the catalyst (1) having the average diameter of 5 mm, while the inlet portion was filled with 650 ml of the catalyst (2) having the average diameter of 8 mm. The temperature of the molten salt was set at 320° C. A gas mixture comprising 9% by volume of propylene, 15% by volume of oxygen, 10% by volume of steam and 66% by volume of nitrogen was introduced for a contact time of 2.2 seconds, and the reaction was carried out. The results are shown in Table 2.

From the results of Table 2, it follows that the temperature of the hot spot is kept low even with the high concentration of the starting material, the selectivity is good and the pressure loss of the catalyst layer is rendered low.

COMPARATIVE EXAMPLE 1

Example 1 was repeated except that the starting gas inlet portion of the reaction pipe was filled with a mixture of the catalyst (1) and alumina balls each having a diameter of 5 mm at a volume ratio of about 2:1. The results are shown in Table 2.

From the results of Table 2, it becomes apparent that the temperature of the hot spot is quite high at the upstream side, the pressure loss is great and the selectivity is low.

EXAMPLE 2

Example 1 was repeated except that the contact time was changed into 1.6 seconds. The results are shown in Table 2.

From the results of Table 2, it can be understood that even when the space velocity is raised to improve productivity, the object of this invention can be achieved.

EXAMPLE 3

A catalyst (3) was prepared in the same way as in Referential Example 1 except that the resulting powder was pelletized to form cylindrical pellets each having a diameter of 5 mm and a height of 5 mm and the pellets were burned at 460° C. for 6 hours under an atmosphere of air. Likewise, a catalyst (4) was prepared by forming cylindrical pellets each having a diameter of 6 mm and a height of 6 mm and burning the pellets at 460° C. for 6 hours; also, a catalyst (5) was prepared by forming cylindrical pellets each having a diameter of 8 mm and a height of 8 mm and burning the pellets at 480° C. for 6 hours under an atmosphere of air.

The same reaction pipe as used in Example 1 except that the diameter of the pipe was 30 mm was filled with 500 ml of the catalyst (5), 450 ml of the catalyst (4) and 900 ml of the catalyst (3) in this order from the starting gas inlet side toward the outlet side.

Then, the reaction was conducted as in Example 1. The results are shown in Table 2.

EXAMPLE 4

A catalyst (6) was prepared as in Referential Example 1 except that the resulting powder was pelletized to form cylindrical pellets each having an average diameter of 6 mm and an average height of 6 mm, and the pellets were burned at 460° C. for 6 hours under an atmosphere of air. Likewise, a catalyst (7) was prepared by forming cylindrical pellets each having a diameter of 8 mm and an average height of 8 mm and burning the pellets at 460° C. for 6 hours in an atmosphere of air; a catalyst (8) was prepared by forming cylindrical pellets each having an average diameter of 10 mm and an average height of 10 mm and burning the pellets at 480° C. for 6 hours under an atmosphere of air.

A stainless steel (SUS-304) reaction pipe (an inner diameter of 38 mm) provided in its axis with a thermocouple and dipped in a bath of a molten salt was filled with 700 ml of the catalyst (8), 700 ml of the catalyst (7), 500 ml of the catalyst (6) and 1,100 ml of the catalyst (3) in this order from the starting gas inlet side to the outlet side. Into the reaction pipe, a gas mixture comprising 8% by volume of propylene, 14% by volume of oxygen, 10% by volume of steam and 68% by volume of nitrogen and an inert gas was introduced for a contact time of 2.4 seconds, and the reaction was performed. The results are shown in Table 2.

COMPARATIVE EXAMPLE 2

The reaction was run in the same way as in Example 4 except that a catalyst layer composed only of 3,000 ml of the catalyst (7) was used in place of the catalyst layer composed of the four catalysts (8), (7), (6) and (3). The results are shown in Table 2.

From the results of Table 2, it was found that compared with Example 4, the position in which to show the maximum hot spot temperature is shifted to the reaction gas inlet side, the temperature of the hot spot becomes as high as 413° C., and the conversion and the total one-pass yield of acrylic acid and acrolein are decreased.

EXAMPLE 5

A catalyst (11) having an average diameter of 6 mm and a catalyst (12) having an average diameter of 7 mm were prepared as in Referential Example 1 except that the resulting powder was formed to have a spherical shape.

Then, the reaction was conducted as in Example 1 except that the catalysts (11) and (12) were used instead of the catalysts (1) and (2). The results are shown in Table 2.

From the results of Table 2, it follows that even when the reaction temperature is higher than in Example 1, the good yields are obtained.

COMPARATIVE EXAMPLE 3

The reaction was run as in Example 5 except that 1,300 ml of the catalyst (12) alone was filled. As a result, at the reaction temperature of 330° C., the conversion of propylene was 93.4 mol %, the total one-pass yield of acrolein and acrylic acid 88.7 mol %, and the hot spot temperature 393° C. respectively.

COMPARATIVE EXAMPLE 4

The reaction was conducted as in Example 5 except that 1,300 of the catalyst (11) alone was filled. Though the reaction temperature was lowered to 295° C., the hot spot temperature was raised, and the reaction could not continue.

EXAMPLE 6

The reaction pipe having an inner diameter of 25 mm was filled with 300 ml of the catalyst (2) in Example 1, 300 ml of the catalyst (11) in Example 5 and 600 ml of the catalyst (1) in Example 1 in this order from the starting gas inlet side toward the outlet side.

The reaction was run as in Example 1 except that the molten salt temperature was changed into 315° C. The results are shown in Table 2.

From the results of Table 2, it follows that the good results are obtained by increasing the number of the reaction zones.

EXAMPLE 7

A catalyst (13) having an average diameter of 5 mm was prepared as in Referential Example 1 except that the amount of cobalt nitrate was changed, cesium nitrate was used instead of potassium hydroxide and burning was conducted at 500° C. for 6 hours while passing an air stream. The catalyst (13) had the following composition (at an atomic ratio except oxygen).

$Mo_{10}W_2Bi_1Fe_1Co_7Cs_{0.06}Si_{1.5}$

Moreover, a catlyst (14) was prepared as in Referential Example 1 except that the same powder as above was formed to have an average diameter of 8 mm and burning was then conducted at 520° C. for 6 hours.

The same reactor as used in Example 1 was filled in the starting gas inlet portion with 750 ml of the catalyst (14) and in the outlet portion with 750 ml of the catalyst (13). A gas mixture comprising 7% by volume of isobutylene, 15% by volume of oxygen, 10% by volume of steam and 68% by volume of nitrogen was introduced at a molten salt temperature of 350° C. for a contact time of 2.2 seconds was introduced therein, and the reaction was carried out. The results are shown in Table 3.

COMPARATIVE EXAMPLE 5

The reaction was conducted as in Example 7 except that 1,500 ml of the catalyst (13) alone was filled. Then, a violent reaction occurred in the catalyst layer.

COMPARATIVE EXAMPLE 6

The reaction was conducted as in Example 7 except that 750 ml of a mixture comprising the catalyst (13) and a porcelain Raschig ring having an average diameter of 5 mm and an average length of 5 mm at a volume ratio of 2:1 was filled in the starting gas inlet portion and the catalyst (13) was filled in the outlet portion. The results are shown in Table 3.

EXAMPLE 8

A catalyst (15) was prepared as in Example 3 like the catalyst (5) except that the resulting powder was pelletized to form ring-like pellets each having an outer diameter of 8 mm, a ring length of 8 mm and a wall thickness of 3 mm (an inner diameter of 2 mm).

The reaction was run as in Example 3 except that the catalyst (15) was used instead of the catalyst (5). The results are shown in Table 2.

EXAMPLE 9

A powder was formed as in Referential Example 1 except that the amount of cobalt nitrate was changed, nickel nitrate was added, rubidium nitrate and barium nitrate were used instead of potassium hydroxide and cerium oxide was added at the last stage of preparing a slurry.

This powder was formed into spheres each having a diameter of 8 mm and a diameter of 5 mm. There resulted catalysts (16) and (17). These catalysts were burned at 475° C. for 7 hours while passing air.

The two catalysts had the following compositions (at an atomic ratio except oxygen).

$Mo_{10}W_2Bi_1Fe_1Co_3Ni_2Rb_{0.1}$ $Ba_{0.1}Ce_{0.5}Si_{1.5}$

The reaction was carried out as in Example 1 except that the catalyst (16) was used instead of the catalyst (2) and the catalyst (17) instead of the catalyst (1) respectively. The results are shown in Table 2.

TABLE 1

| | Diameter of a spherical catalyst (mm) | Concentration of propylene (vol. %) | Molten salt temp. (°C.) | Conversion of propylene (mol %) | Selectivity (mol %) acrolein | Selectivity (mol %) acrylic acid | Total one-pass yield of acrolein + acrylic acid (mol %) | Temperature of a hot spot (°C.) | Pressure loss (mmHg) |
|---|---|---|---|---|---|---|---|---|---|
| REx. 1 | 8 | 6 | 320 | 88.3 | 87.2 | 9.3 | 85.2 | 366 | 85 |
| REx. 2 | 8 | 9 | 320 | 81.6 | 88.7 | 8.8 | 79.6 | 389 | 87 |
| REx. 3 | 5 | 6 | 310 | 98.3 | 86.6 | 9.6 | 94.5 | 381 | 180 |
| REx. 4 | 5 | 9 | 290 | * | * | * | * | — | 173 |

| | Diameter of a spherical catalyst (mm) | Concentration of isobutylene (vol. %) | Molten salt temp. (°C.) | Conversion of isobutylene (mol %) | Selectivity (mol %) | one-pass yield (mol %) | Temperature of a hot spot (°C.) | Pressure loss (mmHg) |
|---|---|---|---|---|---|---|---|---|
| REx. 5 | 5 | 7 | 350 | * | * | * | — | 192 |

REx.: Referential Example
*The reaction could not continue.

TABLE 2

| | Catalyst filling method (inlet → outlet) (ml) 1st layer | 2nd layer | 3rd layer | 4th layer | Diameter of a reaction pipe (mm) | Concentration of propylene (mol %) | Contact time (sec.) | Reaction temperature (°C.) |
|---|---|---|---|---|---|---|---|---|
| Ex. 1 | (2) 650 | (1) 650 | — | — | 25 | 9 | 2.2 | 320 |
| CEx. 1 | (X) 650 | (1) 650 | — | — | 25 | 9 | 2.2 | 320 |
| Ex. 2 | (2) 650 | (1) 650 | — | — | 25 | 9 | 1.6 | 330 |
| Ex. 3 | (5) 500 | (4) 450 | (3) 900 | — | 30 | 9 | 2.2 | 320 |
| Ex. 4 | (8) 700 | (7) 700 | (6) 500 | (3) 1100 | 38 | 8 | 2.4 | 320 |
| CEx. 2 | (7) 3000 | — | — | — | 38 | 8 | 2.4 | 325 |
| Ex. 5 | (12) 650 | (11) 650 | — | — | 25 | 9 | 2.2 | 325 |
| CEx. 3 | (12) * | | | | 25 | 9 | 2.2 | 330 |
| CEx. 4 | (11) ** | | | | 25 | 9 | 2.2 | 295 |
| Ex. 6 | (2) 300 | (11) 300 | (1) 600 | — | 25 | 9 | 2.2 | 315 |
| Ex. 8 | (15) 500 | (4) 750 | (3) 900 | — | 30 | 9 | 2.2 | 320 |
| Ex. 9 | (16) 650 | (17) 650 | — | — | 25 | 9 | 2.2 | 325 |

| | Conversion of propylene (mol %) | Selectivity (mol %) acrolein | Selectivity (mol %) acrylic acid | Total one-pass yield of acrolein + acrylic acid (mol %) | Temperature of a hot spot (°C.) |
|---|---|---|---|---|---|
| Ex. 1 | 97.8 | 85.1 | 10.7 | 93.7 | 387/(1) |
| CEx. 1 | 97.7 | 81.2 | 12.6 | 91.6 | 418/(1) |
| Ex. 2 | 97.4 | 83.6 | 11.6 | 92.7 | 396/(1) |

TABLE 2-continued

| | | | | | |
|---|---|---|---|---|---|
| Ex. 3 | 98.0 | 81.9 | 12.5 | 92.5 | 398/(1) |
| Ex. 4 | 98.3 | 78.2 | 15.3 | 91.9 | 398/(2) |
| CEx. 2 | 91.2 | 87.1 | 9.4 | 88.0 | 413/(1) |
| Ex. 5 | 97.7 | 85.6 | 9.8 | 93.2 | 392/(1) |
| CEx. 3 | 93.4 | 86.5 | 8.5 | 88.7 | 393 |
| CEx. 4 | reaction impossible | | | | abnormally increased |
| Ex. 6 | 98.0 | 85.7 | 10.0 | 93.8 | 389/(2) |
| Ex. 8 | 98.3 | 82.6 | 12.0 | 93.0 | 395/(1) |
| Ex. 9 | 97.5 | 84.8 | 10.7 | 93.1 | 391/(1) |

Ex.: Example
CEx.: Comparative Example
(X): Mixture of 430 ml of catalyst (1) and 220 ml of alumina balls
*: Single layer of catalyst (12) (1300)
**: Single layer of catalyst (11) (1300)
"387/(1)" in Temperature of a hot spot indicates that a reaction zone showing the highest hot spot temperature is a 1st layer and its temperature is 387° C.
"(2) 650" in Catalyst filling method indicates that catalyst (2) was filled in an amount of 650 ml.

TABLE 3

| | Catalyst filling method (inlet → outlet) (ml) | | | | Diameter of a reaction pipe (mm) | Concentration of isobutylene (mol %) | Contact time (sec.) | Reaction temperature (°C.) |
|---|---|---|---|---|---|---|---|---|
| | 1st layer | 2nd layer | 3rd layer | 4th layer | | | | |
| Ex. 7 | (14) 750 | (13) 750 | — | — | 25 | 7 | 2.2 | 350 |
| CEx. 5 | (13) 1500 | — | — | — | 25 | 7 | 2.2 | 350 |
| CEx. 6 | (Y) 750 | (13) 750 | — | — | 25 | 7 | 2.2 | 350 |

| | Conversion of isobutylene (mol %) | Selectivity (mol %) | | Total one-pass yield of MAC + MAA (mol %) | Temperature of a hot spot (°C.) |
|---|---|---|---|---|---|
| | | MAC | MAA | | |
| Ex. 7 | 98.3 | 83.2 | 3.8 | 85.5 | 402/(1) |
| CEx. 5 | * | — | — | — | — |
| CEx. 6 | 98.2 | 81.1 | 4.5 | 84.1 | 427/(2) |

Y: Mixture of 430 ml of catalyst (13) and 220 ml of Raschig ring
*: A violent reaction occurred.
MAC: methacrolein
MAA: methacrylic acid
The type and the amount of the catalyst in Catalyst filling method and Temperature of a hot spot are the same as in Table 2.

TABLE 4

| Catalyst No. | Shape | Size (mm) R | L | L' | Occupied volume (mm³) |
|---|---|---|---|---|---|
| (1) | spherical | 5 | — | — | 65.45 |
| (2) | spherical | 8 | — | — | 268.05 |
| (3) | cylindrical | 5 | 5 | — | 98.17 |
| (4) | cylindrical | 6 | 6 | — | 169.65 |
| (5) | cylindrical | 8 | 8 | — | 402.12 |
| (6) | cylindrical | 6 | 6 | — | 169.65 |
| (7) | cylindrical | 8 | 8 | — | 402.12 |
| (8) | cylindrical | 10 | 10 | — | 785.40 |
| (11) | spherical | 6 | — | — | 113.10 |
| (12) | spherical | 7 | — | — | 179.59 |
| (13) | spherical | 5 | — | — | 65.45 |
| (14) | spherical | 8 | — | — | 268.08 |
| (15) | ring-like | 8* | — | — | 402.12 |
| (16) | spherical | 8 | — | — | 268.08 |
| (17) | spherical | 5 | — | — | 65.45 |

R: average diameter
L: average length
L': average ring height
*: average outer diameter (R')

EXAMPLES 10-1 to 10-8 and COMPARATIVE EXAMPLES A to P

Various catalysts were prepared as in Referential Example 1 except that the composition was changed as shown in Table 5-1. Each of the catalysts was filled in a reaction pipe in either a double layer (Examples 10-1 to 10-8) or a single layer (Comparative Examples A to P), and the reaction was run as in Example 1. The results are shown in Table 5-2.

TABLE 5-1

| | Composition ratio of a catalyst | | | | | | | | Filling method |
|---|---|---|---|---|---|---|---|---|---|
| | Mo | W | Bi | Fe | A | B | C | D | |
| EX. 10-1 | | | | | Co 3 | K 0.1 | | | Double layer: 650 ml (8 mmφ) + 650 ml (5 mmφ) |
| CEx. A | 10 | 2 | 1.5 | 2.0 | | | Ce 2 | Si 2.0 | Single layer: 1300 ml (8 mmφ) |
| CEx. B | | | | | Ni 3 | Cs 0.05 | | | Single layer: 1300 ml (5 mmφ) |
| EX. 10-2 | | | | | Co 1 | Na 0.1 | | | Double layer: 650 ml (8 mmφ) + 650 ml (5 mmφ) |
| CEx. C | 12 | 0 | 1.8 | 1.0 | | | — | Al 3.0 | Single layer: 1300 ml (8 mmφ) |
| CEx. D | | | | | Ni 5 | Rb 0.05 | | | Single layer: 1300 ml (5 mmφ) |
| EX. 10-3 | | | | | Co 3 | Na 0.1 | | Si 1.5 | Double layer: 650 ml (8 mmφ) + 650 ml (5 mmφ) |
| CEx. E | 12 | 0 | 1.0 | 2.0 | | | P 0.1 | | Single layer: 1300 ml (8 mmφ) |
| CEx. F | | | | | Ni 1 | Ba 0.1 | | Ti 0.5 | Single layer: 1300 ml (5 mmφ) |
| EX. 10-4 | | | | | Co 2 | K 0.1 | | | Double layer: 650 ml (8 mmφ) + 650 ml (5 mmφ) |
| CEx. G | 11 | 1 | 0.5 | 1.5 | | | Mn 0.5 | Si 1.5 | Single layer: 1300 ml (8 mmφ) |

TABLE 5-1-continued

| | Composition ratio of a catalyst | | | | | | | Filling method |
|---|---|---|---|---|---|---|---|---|
| | Mo | W | Bi | Fe | A | B | C | D | |
| CEx. H | | | | | Ni 4 | Ca 0.05 | | | Single layer: 1300 ml (5 mmφ) |
| EX. 10-5 | | | | | | K 0.05 | | Ti 1.0 | Double layer: 650 ml (8 mmφ) + 650 ml (5 mmφ) |
| CEx. I | 11 | 1 | 2.0 | 1.0 | Co 6 | | P 0.1 | | Single layer: 1300 ml (8 mmφ) |
| CEx. J | | | | | | Cs 0.01 | | Zr 0.5 | Single layer: 1300 ml (5 mmφ) |
| EX. 10-6 | | | | | Co 5 | Na 0.1 | | | Double layer: 650 ml (8 mmφ) + 650 ml (5 mmφ) |
| CEx. K | 12 | 0 | 2.0 | 1.5 | | | Zn 1 | Si 1.5 | Single layer: 1300 ml (8 mmφ) |
| CEx. L | | | | | Ni 3 | Rb 0.05 | | | Single layer: 1300 ml (5 mmφ) |
| EX. 10-7 | | | | | Co 6 | | | Si 3.0 | Double layer: 650 ml (8 mmφ) + 650 ml (5 mmφ) |
| CEx. M | 10 | 2 | 1.0 | 1.5 | | Cs 0.3 | — | | Single layer: 1300 ml (8 mmφ) |
| CEx. N | | | | | Ni 3 | | | Al 2.0 | Single layer: 1300 ml (5 mmφ) |
| EX. 10-8 | | | | | | Na 0.1 | | Si 2.0 | Double layer: 650 ml (8 mmφ) + 650 ml (5 mmφ) |
| CEx. O | 10 | 2 | 1.5 | 1 | Ni 4 | | Mn 1 | | Single layer: 1300 ml (8 mmφ) |
| CEx. P | | | | | | Rb 0.05 | | Ti 1.0 | Single layer: 1300 ml (5 mmφ) |

TABLE 5-2

| | Reaction temp. (°C.) | Conversion of propylene (mol %) | Selectivity (mol %) | | Total one-pass yield of acrolein and acrylic acid (mol %) | Temperature of a hot spot (°C.) |
|---|---|---|---|---|---|---|
| | | | acrolein | acrylic acid | | |
| EX. 10-1 | 320 | 97.5 | 84.0 | 10.9 | 92.5 | 388 |
| CEx. A | 330 | 88.7 | 86.5 | 8.5 | 84.3 | 394 |
| CEx. B | 320 | 98.7 | 73.8 | 17.2 | 89.8 | 410 |
| EX. 10-2 | 320 | 98.0 | 92.4 | 12.3 | 92.8 | 392 |
| CEx. C | 320 | 87.4 | 88.0 | 7.5 | 83.5 | 385 |
| CEx. D | 295 | | reaction impossible | | | abnormally increased |
| EX. 10-3 | 320 | 98.3 | 83.0 | 11.2 | 92.6 | 394 |
| CEx. E | 320 | 91.0 | 86.7 | 8.5 | 86.6 | 381 |
| CEx. F | 295 | | reaction impossible | | | abnormally increased |
| EX. 10-4 | 330 | 97.3 | 84.0 | 10.6 | 92.0 | 397 |
| CEx. G | 340 | 90.2 | 86.0 | 9.0 | 85.7 | 398 |
| CEx. H | 320 | 98.0 | 77.4 | 14.6 | 90.2 | 412 |
| EX. 10-5 | 315 | 97.8 | 81.0 | 13.9 | 92.8 | 392 |
| CEx. I | 330 | 89.5 | 87.0 | 8.2 | 85.2 | 389 |
| CEx. J | 305 | 98.5 | 75.5 | 15.7 | 90.2 | 403 |
| EX. 10-6 | 320 | 98.3 | 82.2 | 12.4 | 93.0 | 395 |
| CEx. K | 330 | 90.4 | 86.8 | 8.3 | 86.0 | 381 |
| CEx. L | 295 | | reaction impossible | | | abnormally increased |
| EX. 10-7 | 320 | 97.8 | 85.0 | 10.3 | 93.2 | 387 |
| CEx. M | 320 | 89.1 | 88.0 | 7.5 | 85.5 | 377 |
| CEx. N | 310 | 98.5 | 77.0 | 13.8 | 89.4 | 408 |
| EX. 10-8 | 320 | 97.3 | 82.8 | 12.3 | 92.5 | 398 |
| CEx. O | 330 | 87.6 | 88.5 | 7.3 | 83.9 | 392 |
| CEx. P | 315 | 97.8 | 79.5 | 14.0 | 91.4 | 413 |

What we claim is:

1. A process for producing an unsaturated aldehyde and an unsaturated acid comprising catalytically oxidizing propylene or at least one compound selected from isobutylene, tert.-butyl alcohol and methyl-tert.-butyl ether in a gaseous phase with molecular oxygen or a molecular oxygen-containing gas using a fixed bed multipipe reactor, wherein (a) a plurality of composite oxides different in occupied volume, represented by formula

$$Mo_a W_b Bi_c Fe_d A_e B_f C_g D_h O_x \quad (I)$$

wherein Mo denoted molybdenum; W denotes tungsten; Bi denotes bismuth; Fe denotes iron; A denotes at least one element selected from cobalt and nickel; B denotes at least one element selected from an alkali metal, an alkaline earth metal and thallium; C denotes at least one element selected from phosphorus, tellurium, arsenic, boron, niobium, antimony, tin, lead, manganese, cerium and zinc; D denotes at least one element selected from silicon, aluminum, titanium and zirconium; O denotes oxygen; a, b, c, d, e, f, g, h and x denote numbers of atoms of Mo, W, Bi, Fe, A, B, C, D and O; a=2 to 12, b=0 to 10 and a+b=12, c=0.1 to 10, d=0.1 to 10, e=2 to 20, f=0.005 to 3, g=0 to 4, h−0.5 to 30 and x=value determined by an oxidized state of each element, are used as catalysts, (b) a plurality of reaction zones are provided along an axial direction in each reaction pipe of the fixed bed multipipe reactor, and (c) the plurality of the catalysts different in occupied volume are filled in the plurality of the reaction zones such that the occupied volumes become lower from the starting gas inlet side to the outlet side.

2. The process of claim wherein propylene is catalytically oxidized in a gaseous phase to produce acrolein and acrylic acid.

3. The process of claim 1 wherein at least one compound selected from isobutylene, tert.-butyl alcohol and methyl-tert.-butyl ether is catalytically oxidized in a gaseous phase to produce methacrolein methacrylic acid.

4. The process of claim 1, wherein for any two adjacent reaction zones, the occupied volume of the composite oxide of the reaction zone closer to the starting gas inlet side is designated $V_1$ and the occupied volume of the composite oxide of the reaction zone closer to the outlet side is designated $V_2$ and $V_1/V_2$ is 1.2/1 to 64/1.

5. The process of claim 4, wherein $V_1/V_2$ is 1.3/1 to 27/1.

6. The process of claim 1, wherein the oxidation is carried out at a temperature of 250° to 450° C.

7. The process of claim 1, wherein the oxidation is carried out at a pressure of from atmospheric pressure to 10 atmospheres.

8. The process of claim 1, wherein the oxidation is carried out at a space velocity of 300 to 5,000 hr.$^{-1}$.

* * * * *